(12) United States Patent
Wang et al.

(10) Patent No.: US 7,677,536 B2
(45) Date of Patent: Mar. 16, 2010

(54) HUMIDIFIER WITH CONTROLLED HEATED SCENT MECHANISM

(75) Inventors: Zhijing Wang, Clifton Park, NY (US); Linda Hotz, New City, NY (US)

(73) Assignee: Kaz, Incorporated, New York, NY (US)

( * ) Notice: Subject to any disclaimer, the term of this patent is extended or adjusted under 35 U.S.C. 154(b) by 862 days.

(21) Appl. No.: 11/452,149

(22) Filed: Jun. 12, 2006

(65) Prior Publication Data

US 2007/0284765 A1    Dec. 13, 2007

(51) Int. Cl.
*B01D 47/00*    (2006.01)

(52) U.S. Cl. .................... 261/26; 261/104; 261/142; 261/DIG. 65; 261/DIG. 88; 261/DIG. 89

(58) Field of Classification Search ................... 261/26, 261/104, 142, DIG. 65, DIG. 88, DIG. 89
See application file for complete search history.

(56) References Cited

U.S. PATENT DOCUMENTS

| | | | | |
|---|---|---|---|---|
| 4,752,422 A | * | 6/1988 | Uchida et al. | ............... 261/81 |
| 5,519,900 A | | 5/1996 | Gardner | |
| 6,511,531 B1 | * | 1/2003 | Cartellone | ................... 96/222 |
| 2004/0071456 A1 | | 4/2004 | Levine et al. | |
| 2006/0042205 A1 | | 3/2006 | Kalous et al. | |

FOREIGN PATENT DOCUMENTS

JP    11351621    12/1999

* cited by examiner

*Primary Examiner*—Robert A Hopkins
(74) *Attorney, Agent, or Firm*—Stroock & Stroock & Lavan LLP

(57) ABSTRACT

A portable appliance including a humidifier and an electrically heated scent mechanism. The heated scent mechanism includes a scent generator and an electrical heating element. The heating element and humidifier may be independently controllable such that the appliance can serve as either a humidifier or air-freshener, individually or simultaneously.

18 Claims, 4 Drawing Sheets

HUMIDIFIER WITH CONTROLLED HEATED SCENT MECHANISM

FIELD OF THE INVENTION

The invention generally relates to humidifiers, and more specifically relates to humidifiers having a heated scent mechanism.

BACKGROUND

The ability to easily and efficiently control indoor environments is highly desirable. For this reason, a number of devices have been developed to control the temperature, humidity, odor and air quality of enclosed environments such as the rooms of a house. In order to control these characteristics, a multiplicity of devices are needed inside the room. This causes a problem in instances where there are a limited number of outlets in the room. Further, the number of devices needed to control all of the desired environmental characteristics in a room can result in an unsightly mess and crowding of the room.

In temperate climates controlling humidity can be very important. During the winter and the months surrounding the winter, a lack of humidity in the air can cause significant discomfort to people. Humidifiers are a typical device used to control humidity. During these same months, many people develop colds and have sinus and chest congestion. One method for treating congestion and colds is by dispersing medicinal vapors in the air, for example menthol. The medicinal vapors help reduce cold symptoms as well as sinus and chest congestion. Medicinal vapors can be dispersed by scent generators, similar to air fresheners.

Humidifiers including means for generating a scent have been developed but have various drawbacks. These humidifiers include an air freshener to disperse an aesthetic scent in to the environment. Known humidifiers having an air freshening capability include humidifiers with scented objects disposed in an air path generated by a fan of the humidifier. The scented object continuously diffuses a scent into the air and the fan blows the scent into the surrounding environment. Another known device is a vaporizing humidifier which holds a liquid scent which is heated by the vaporized water. The scent dissipates into the atmosphere as it is heated. Both of these devices, however, are limited because the humidifier and air freshener cannot act independently and the scent is dispersed by the airflow or vapor created upon activation of the humidifier. Further, the first device described above has an additional drawback in that the air-freshening mechanism continuously diffuses scent into the air. This type of air-freshener cannot be turned off or deactivated. Even without the fan, natural air currents will spread the scent throughout the room.

Thus, there is a need for a combination humidifier and scent generator which allows each of the scent generating and humidifying component to operate independently.

SUMMARY OF THE INVENTION

The present invention provides a humidifier with a heated scent mechanism. The humidifier may be a portable humidifier which plugs into an electrical outlet. The humidifier may be any type of humidifier, including evaporative wick-type, impeller type, warm-mist type and ultrasonic humidifiers, as well as vaporizing humidifiers.

The scent mechanism used with the humidifier in the present invention may include any object or liquid that is capable of generating a scent. For example, the mechanism may operate with an air-freshener, deodorizer, scented oil or perfume. The mechanism is not limited to any of these examples so long as it produces a scent when it is heated. The exemplary mechanism described in the foregoing is referred to as a scent generator, which is meant to encompass all of the aforementioned examples.

The humidifier includes a receptacle for the scent generator. The scent generator may include a scented solid unit or a carrier such as a woven or non woven pad containing menthol or an oil based scent. The scent generator is either placed in the receptacle, or may be a scented liquid that is poured into the receptacle. Adjacent the receptacle is an electrical heating element. Upon activation, current flows through the heating element causing the element to rise in temperature. Heat is transferred from the heating element to the receptacle, in turn heating the scent generator which promotes evaporation and dispersion of the scent into the air.

The humidifier may also include a control panel with controls for independently or simultaneously controlling the humidifier and the heated scent mechanism. Thus, either the heated scent mechanism or the humidifier may be operating while the other is not, or both may be in operation at the same time.

BRIEF DESCRIPTION OF THE FIGURES

These and other objects and features of the invention will become more apparent by referring to the drawings, in which.

DETAILED DESCRIPTION OF THE PREFERRED EMBODIMENTS

Figure 1:
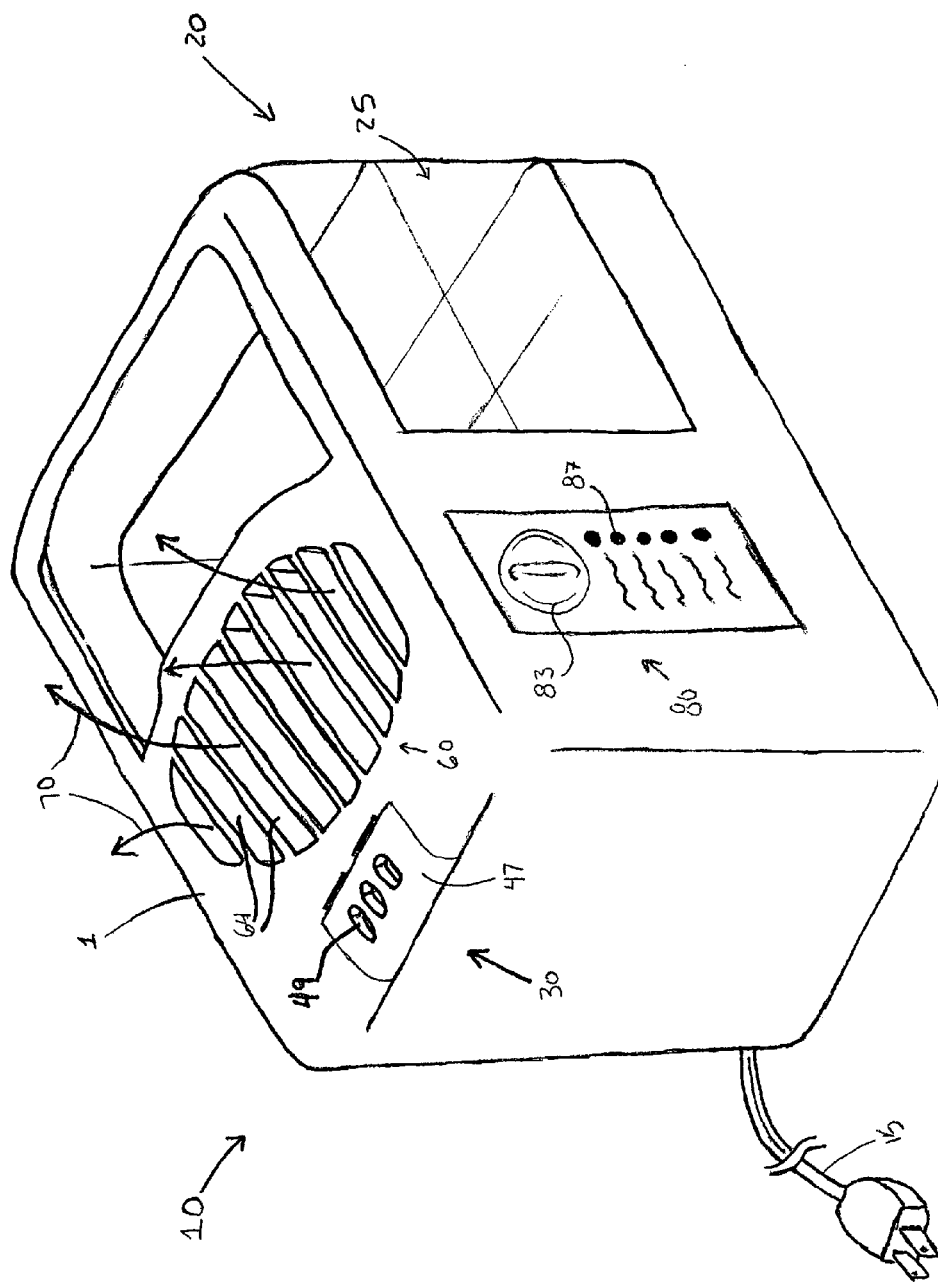
FIG. 1 is a perspective view of a humidifier in accordance with a first embodiment of the present invention.
Figure 2:
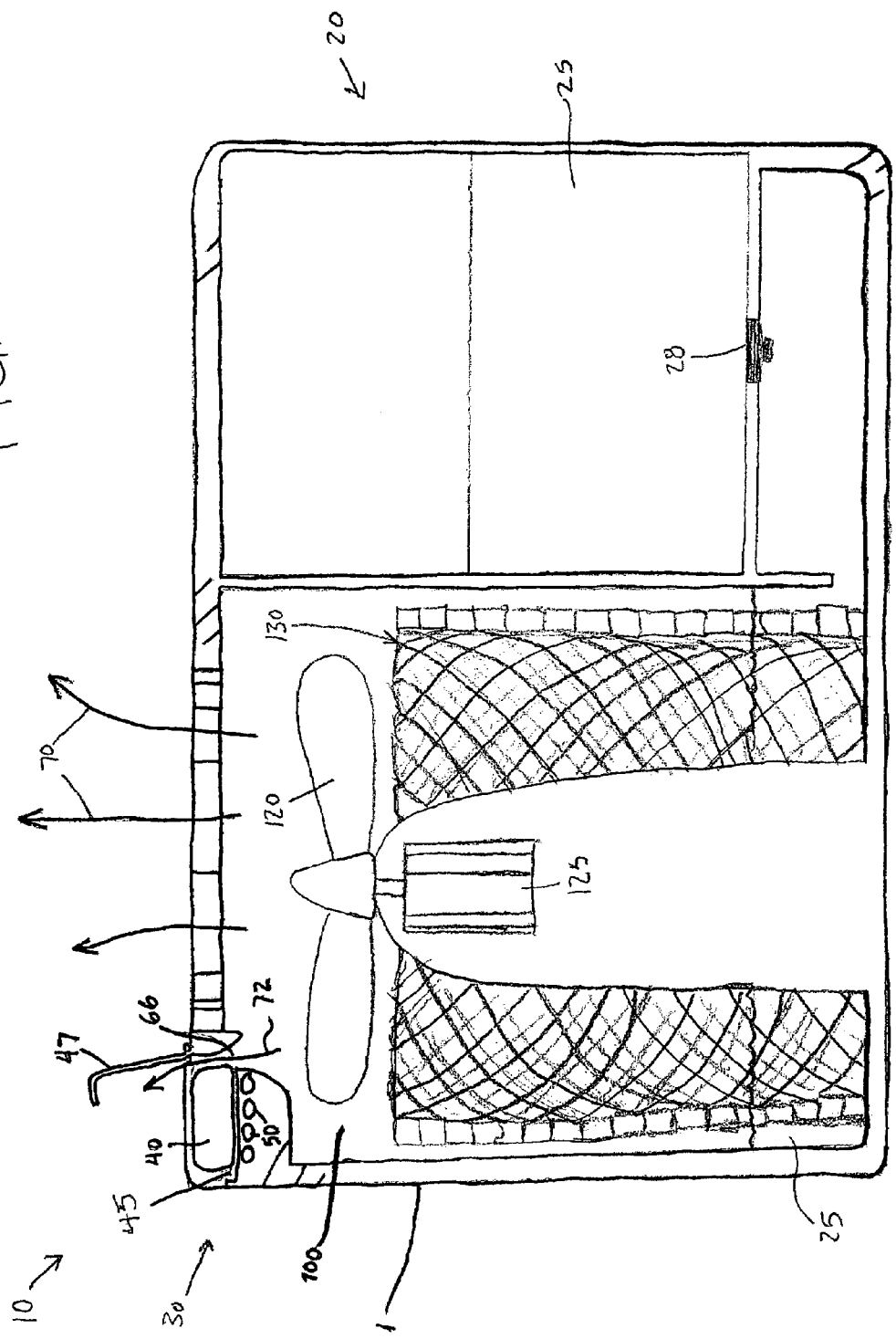
FIG. 2 is a cross-sectional view of the humidifier shown in FIG. 1.

One embodiment of the present invention is shown in FIGS. 1 and 2. Humidifier 10 includes a housing 1. A water tank 20 is connected to the housing. The water tank 20 is portable, and may be removed from the housing. The housing 1 includes a vent 60 in the form of a grill providing a passage 64 from an inner portion 100 of humidifier 10 to its surroundings. In operation of the humidifier 10, a flow 70 of humidified air passes through passage 64 to humidify the surrounding environment. In the case of a vaporizing humidifier, the flow 70 may be steam.

The inner portion 100 of the humidifier 10 includes a fan 120 driven by a motor 125. A wick 130 is held within the inner portion 100 and absorbs water 25 from the bottom of the inner portion 100. The water 25 is fed to the inner portion 100 from the water tank 20 by a valve 28. The valve 28 regulates the amount of water in the inner portion 100 of the housing 1. As the fan 120 rotates, air is drawn over wick 130. Water 25 is evaporated from wick 130 and the air drawn by fan 120 becomes the flow 70 of humidified air. The amount of humidification supplied by humidifier 10 is controlled by fan 120. When the fan 120 rotates faster it generates more flow 70, which increases the amount of water 25 that is dispersed in the surrounding environment.

Humidifier 10 also includes heated scent mechanism 30 formed of a scent generator 40 and a heating element 50. The scent generator 40 is placed in a receptacle 45 in the housing. The scent generator 40 may be in the form of a solid unit or may be a liquid poured into receptacle 45. The solid unit form of scent generator 40 may be made of a gel-type air freshener held in a container. Further, the scent generator 40 may include oil or alcohol based scent ingredients. The scent generator 40 may have a purely aesthetic scent, such as a floral or citrus scent, or the scent may have medicinal properties. The medicinal embodiment of scent generator 40 may include menthol, a vitamin solution, beauty lotion or other substances.

The heating element 50 is electrically activated and positioned within the housing adjacent the receptacle 45, such that heating element 50 warms scent generator 40 during operation. As the temperature of scent generator 40 rises it evaporates and the scent is dispersed into the air. Heating element 50 may be formed of a heating coil or a positive temperature coefficient (PTC) element 51. The term heating coil, as used herein, refers to a metallic element of any shape that increases in temperature as current is passed through it.

Figure 3:
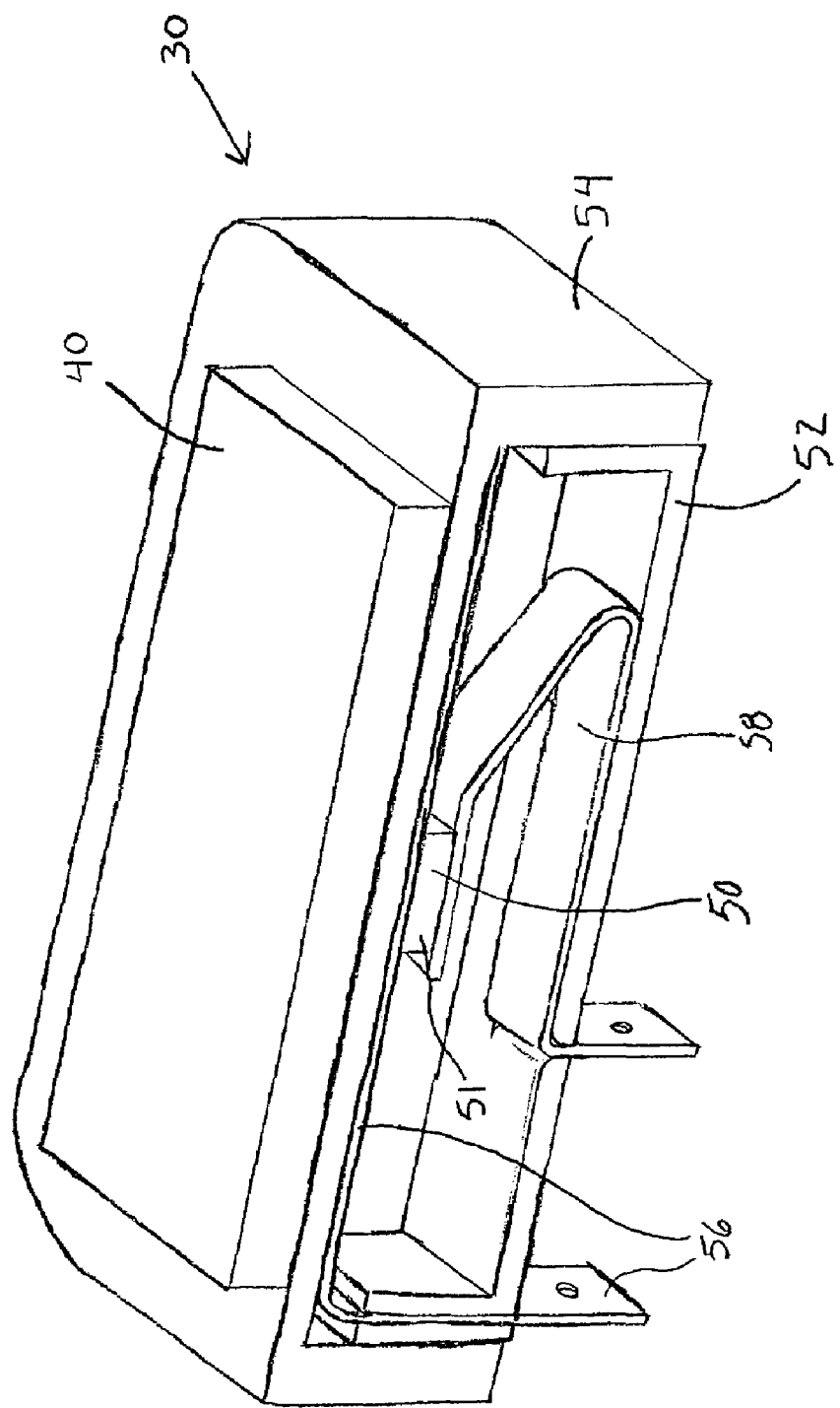
FIG. 3 is a perspective cross-sectional view of a heated scent mechanism in accordance with the present invention.

FIG. 3 shows an exemplary embodiment of heated scent mechanism 30 using a PTC element 51 as heating element 50. The heated scent mechanism includes a housing 52 and a top cover 54 that attaches above the housing 52. Scent generator 40 sits above top cover 40. Two electrodes 56 and 58 extend through housing 52 into heated scent mechanism 30. The electrodes 56 and 58 supply PTC element 51 with electricity. First electrode 56 is adjacent top cover 54 just below scent generator 40. PTC element 51 is held against first electrode 56 by second electrode 58 which is under PTC element 51. As current flows through PTC element 51 and electrodes 56 and 58, PTC element 51 rises in temperature. The hot PTC element 51 heats scent generator 40 releasing scent therefrom. As a result of the rise in temperature, the resistance of the PTC element 51 increases. In other words, if the temperature of the PTC element 51 becomes too high, the current will slow or stop and the PTC element 51 will cool down. Consequently, the PTC element 51 is self regulating and will not rise above a maximum temperature. Thus, PTC element 51 controls the scent evaporation rate from scent generator 40 indirectly.

In an alternative embodiment, the heating element 50 including the PTC element may be formed as a combined unit with the scent generator 40. In this case, the heating element 50 and receptacle may each have complementary electrical contacts so that current from the humidifier 10 can flow through the heating element 50.

The receptacle 45 may include a door 47 thereon to conceal the heated scent mechanism 30. The door 47 should have an opening 49 therein to allow the evaporated scent to dissipate into the environment surrounding the housing 1. The door 47 may be formed to match the housing 1. Door 47 may also help reduce heat loss when closed promoting dispersion of the scent. Additionally, door 47 reduces disturbance of scent generator 40 by the flow 70 of humid air or vapor. Accordingly, door 47 helps keep the operation of heated scent mechanism 30 and humidifier 10.

The heated scent mechanism 30 may be positioned in the housing 1 substantially separated from flow 70. In this embodiment, the humidifier 10 and heated scent mechanism 30 operate either together or entirely independently. Alternatively, a second passage 66 may be formed in the heated scent mechanism 30 to allow a second flow 72 to pass over the scent generator 40. The second passage 66 may include a deflector to regulate the second flow 72. The deflector allows the second flow 72 to be selectively directed over the scent generator 40 or blocked from the scent generator 40 as desired.

Figure 4:
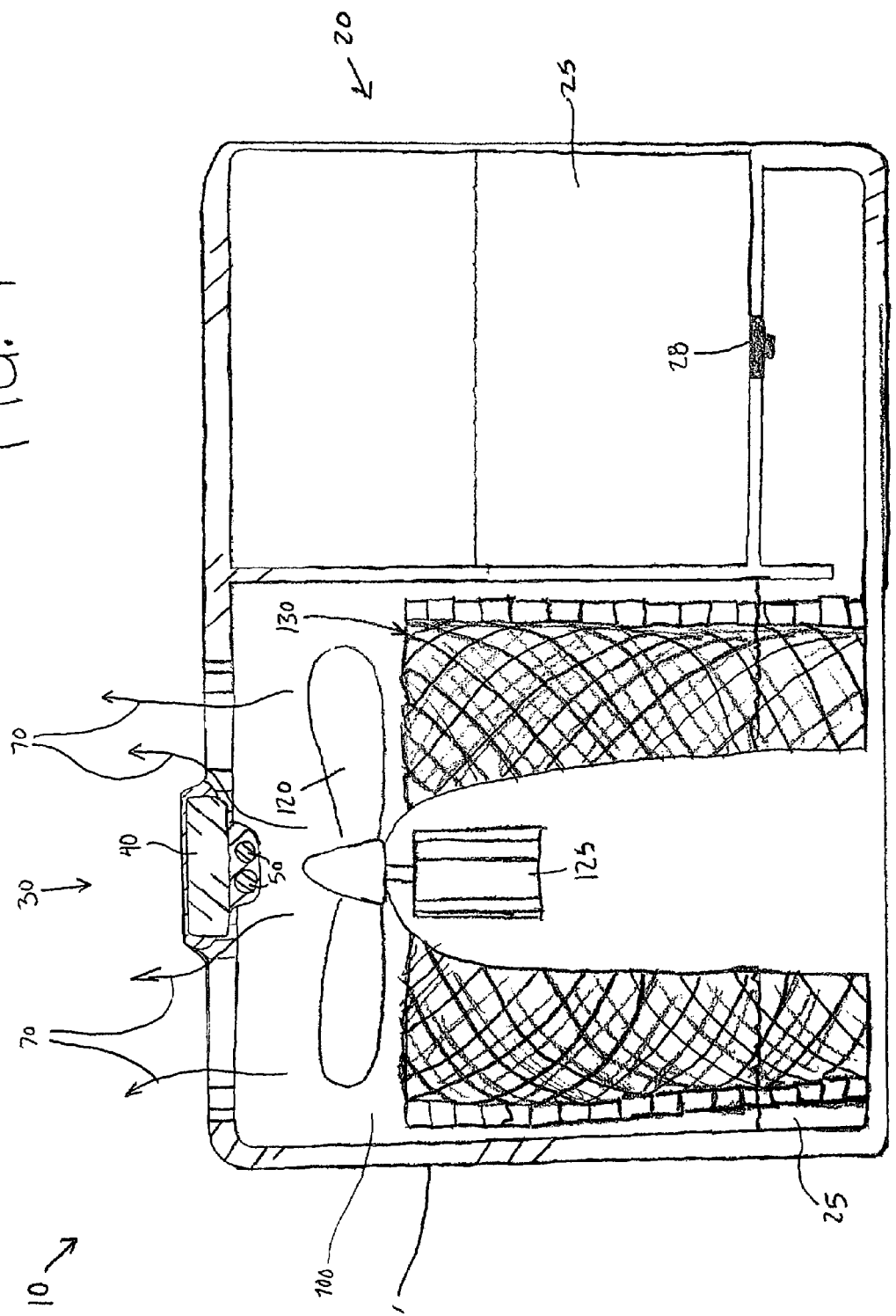
FIG. 4 is a cross-sectional view of another embodiment of a humidifier in accordance with the present invention.

In another embodiment of the invention, as shown in FIG. 4, the heated scent mechanism 30 may be positioned such that flow 70 passes over scent generator 40. This embodiment allows the flow 70 to help dissipate the scent generator 40 to the surrounding atmosphere.

The humidifier 10 is sized for domestic use and is portable such that it can be easily moved from room to room. The humidifier includes an electrical cord and plug 15 which draws current from an outlet for the operation of both the humidifier 10 and heated scent mechanism 30. A control panel 80 is disposed on the housing and includes user controls, such as buttons, switches, dials or the like, for controlling the heated scent mechanism 30 and the humidifier 10. The control panel 80 may include one or more user controls that activate both the heated scent mechanism 30 and the humidifier 10 or it may include one or more first user control 83 for operating the humidifier 10 and one or more second user control 87 for operating the heated scent mechanism 30.

Although the preferred form of the invention has been shown and described, many features may be varied, as will readily be apparent to those skilled in this art. Thus, the foregoing description is illustrative and not limiting, the invention being defined by the following claims.

We claim:

1. A humidifier comprising:
   a housing;
   a water tank coupled to the housing;
   a humidifier mechanism within the housing including a water evaporator and an air circulator;
   a receptacle within the housing and adapted to receive a scent generator;
   an electrical heating element adjacent the receptacle for applying heat to the scent generator;
   a first user control unit controlling the humidifier mechanism; and
   a second user control unit controlling the electrical heating element.

2. The humidifier of claim 1 wherein the air circulator generates a first flow out of the humidifier.

3. The humidifier of claim 2 wherein the first flow passes over the scent generator.

4. The humidifier of claim 2 wherein the first flow is isolated from the scent generator.

5. The humidifier of claim 4 wherein the air circulator generates a second flow which passes over the scent generator.

6. The humidifier of claim 1 wherein the electrical heating element includes an electrical heating coil.

7. The humidifier of claim 1 wherein the electrical heating element includes a PTC element.

8. The humidifier of claim 1 further comprising a door adapted to cover the scent generator.

9. A humidifier comprising:
   a housing;
   a water tank coupled to the housing;
   a humidifier mechanism within the housing including a water vaporizer;
   a receptacle within the housing and adapted to receive a scent generator;
   an electrical heating element adjacent the receptacle for applying heat to the scent generator;
   a first user control unit controlling the humidifier mechanism; and
   a second user control unit controlling the electrical heating element.

10. The humidifier of claim 9 wherein the water vaporizer generates a first flow of vapor out of the humidifier.

11. The humidifier of claim 10 wherein the first flow passes over the air freshener.

12. The humidifier of claim 10 wherein the first flow is isolated from the scent generator.

13. The humidifier of claim 12 wherein the water vaporizer generates a second flow of vapor which passes over the scent generator.

14. The humidifier of claim 9 wherein the electrical heating element includes an electrical heating coil.

15. The humidifier of claim 9 wherein the electrical heating element includes a PTC element.

16. The humidifier of claim 9 further comprising a door adapted to cover the scent generator.

17. A humidifier comprising:
a housing;
a water tank coupled to the housing;
a humidifier mechanism within the housing including a water evaporator and an air circulator;
a receptacle within the housing and adapted to receive a scent generator;
an electrical heating element adjacent the receptacle for applying heat to the scent generator; and
a control unit for separately controlling each of the humidifier mechanism and the electrical heating element.

18. A humidifier comprising:
a housing;
a water tank coupled to the housing;
a humidifier mechanism within the housing including a water vaporizer;
a receptacle within the housing and adapted to receive a scent generator;
an electrical heating element adjacent the receptacle for applying heat to the scent generator; and
a control unit for separately controlling each of the humidifier mechanism and the electrical heating element.

* * * * *